(12) United States Patent
Darbha et al.

(10) Patent No.: US 9,062,019 B2
(45) Date of Patent: Jun. 23, 2015

(54) PROCESS FOR THE EPOXIDATION OF FATTY ACIDS, THEIR ESTERS AND MIXTURES THEREOF

(75) Inventors: Srinivas Darbha, Maharashtra (IN); Jitendra Kumar Satyarthi, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/825,642

(22) PCT Filed: Sep. 22, 2011

(86) PCT No.: PCT/IB2011/002203
§ 371 (c)(1),
(2), (4) Date: Jun. 13, 2013

(87) PCT Pub. No.: WO2012/038811
PCT Pub. Date: Mar. 29, 2012

(65) Prior Publication Data
US 2013/0261322 A1 Oct. 3, 2013

(30) Foreign Application Priority Data
Sep. 23, 2010 (IN) .......................... 2271/DEL/2010

(51) Int. Cl.
*C07D 301/02* (2006.01)
*C07D 301/19* (2006.01)
*B01J 21/04* (2006.01)
(Continued)

(52) U.S. Cl.
CPC ............... *C07D 301/19* (2013.01); *B01J 21/04* (2013.01); *B01J 21/12* (2013.01); *B01J 23/28* (2013.01); *B01J 35/1019* (2013.01); *B01J 35/1038* (2013.01); *B01J 35/1061* (2013.01); *B01J 37/0201* (2013.01); *B01J 37/0207* (2013.01); *B01J 37/28* (2013.01); *C11C 3/006* (2013.01); *B01J 27/19* (2013.01)

(58) Field of Classification Search
CPC ........ C07D 301/19; B01J 21/04; B01J 21/12; B01J 23/28; B01J 35/1019; B01J 35/1038; B01J 37/0201; B01J 37/0207; B01J 37/28; B01J 27/19; B01J 35/1061; C11C 3/006
USPC .......................................... 549/518
See application file for complete search history.

(56) References Cited

U.S. PATENT DOCUMENTS

| 2,810,733 A | 10/1957 | Greenspan |
| 3,351,635 A | 11/1967 | Kollar |

(Continued)

FOREIGN PATENT DOCUMENTS

EP 0 848 016 A2 6/1998

OTHER PUBLICATIONS

Abdullah et al, Epoxidation of Vegetable Oils and Fatty Acids: Catalysts, Methods, Advantages, 2010, 10(15), p. 1545-1553.*

(Continued)

*Primary Examiner* — T. Victor Oh
(74) *Attorney, Agent, or Firm* — Westman, Champlin & Koehler, P.A.

(57) ABSTRACT

The present invention relates to an improved process for preparing mono and poly epoxy functionalized fatty acids, their esters and mixtures thereof using solid catalyst i.e. supported group VIb metal oxide, said support comprising silica, alumina and mixtures thereof, optionally with a promoter from group VA wherein the group VIB metal oxide content in the catalyst is 5-20 wt % of support.

26 Claims, 2 Drawing Sheets (51) Int. Cl.
*B01J 21/12* (2006.01)
*B01J 23/28* (2006.01)
*B01J 35/10* (2006.01)
*B01J 37/02* (2006.01)
*B01J 37/28* (2006.01)
*C11C 3/00* (2006.01)
*B01J 27/19* (2006.01)

(56) References Cited

U.S. PATENT DOCUMENTS 3,489,775 A * 1/1970 Roch et al. .................... 549/529
3,634,464 A * 1/1972 Wulff et al. .................... 549/529
4,215,058 A   7/1980 Jourdan-Laforte
5,081,267 A * 1/1992 Rameswaran et al. ........ 549/529
5,430,161 A   7/1995 Brown et al.

OTHER PUBLICATIONS

Debal et al, Epoxidation of fatty acid methyl esters and organic hydroperoxides and molybdenum oxide, Fat. Sci. Tech., vol. 95, No. 6, 1993, p. 236-239.*
International Search Report and Written Opinion for PCT Application No. PCT/IB2011/002203, dated dated Jan. 23, 2012, 9 pages.

* cited by examiner

PROCESS FOR THE EPOXIDATION OF FATTY ACIDS, THEIR ESTERS AND MIXTURES THEREOF

CROSS-REFERENCE TO RELATED APPLICATION

This Application is a Section 371 National Stage Application of International Application No. PCT/IB2011/002203, filed 22 Sep. 2011 and published as WO2012/038811 on 29 Mar. 2012, in English, the contents of which are hereby incorporated by reference in their entirety.

FIELD OF THE INVENTION

The present invention relates to an improved process for the epoxidation of fatty acids, their esters and mixtures thereof.

Present invention further relates to an improved process for preparing epoxy functionalized fatty acids, their esters and mixtures thereof, which comprises contacting fatty acids, their esters or mixtures thereof with a peroxide in the presence of a solid catalyst and separation of the product epoxide from the reaction mixture.

BACKGROUND OF THE INVENTION

References may be made to Journals "Biermann et al., Angew. Chem. Int. Ed. Year 2000, Vol. 39, pp. 2206-2224" and Seniha Gtiner et al., Prog. Polym. Sci. Year 2006, Vol. 31, pp. 633-670", wherein use of fatty epoxides as plasticizers that are compatible with polyvinyl chloride (PVC) and as stabilizers for PVC resins to improve flexibility, elasticity and toughness and to impart stability of polymer towards heat and UV radiation was disclosed.

Today one of the most important epoxidized vegetable oils is epoxidized soybean oil. Its worldwide production is about 200,000 tons/year.

References may be made to U.S. Pat. No. 2,810,733 and U.S. Pat. No. 4,215,058 wherein epoxidation of vegetable oils is carried out with a mixture of formic acid/hydrogen peroxide or peracids. This process leads to high amount of waste, by-products. It also causes several concerns about safety and engenders corrosion problems that are interrelated to the percarboxylic acids used. More environmentally friendly and cleaner synthetic route than the non-ecofriendly conventional process is highly desirable.

References may be made to Journals "Orellana-Coca et al., J. Mol. Catal. B: Enzym., Year 2007, Vol. 44, pp. 133-137; Warwel and Klass J. Mol. Catal. B: Enzym., Year 1995, Vol. 1, pp. 29-35; Piazza et al., J. Mol. Catal. B: Enzym. Year 2003, Vol. 21, pp. 143-151" wherein immobilized enzymes (lipase, oat sead peroxygenase, etc.) exhibit good performance for this reaction but they are very sensitive to the kind of substrate employed and they are often not suitable for obtaining high yields in polyepoxidized products. Homogeneous catalysts including methyltrioxorhenium and peroxophosphotungstates (U.S. Pat. No. 5,430,161; Kozhevnikov et al., J. Mol. Catal. A: Chem., Year 1998, Vol. 134, pp. 223-228; Jiang et al., J. Am. Oil Chem. Soc., Year 2010, Vol. 87, pp. 83-91) show good catalytic activity with hydrogen peroxide as oxidant. Difficulty in catalyst separation and reuse are the issues with those homogeneous catalysts. Often, additional nitrogen-based co-catalysts (substituted imidazoles, pyridine, etc) need to be used along with the homogenous catalysts to obtain high conversion and epoxide selectivity.

Heterogeneous catalysts are advantageous as they can be separated easily from the reaction mixtures. Ti-grafted silica catalysts have been examined for the liquid phase oxidation of a mixture of fatty acid methyl esters. While these catalysts are active, they require very long reaction times (24 hr or more) and the epoxide yields are not as high as those obtained in the industrial processes (Rios et al., J. Catal. Year 2005, Vol. 232, pp. 19-26; Campanella et al., Green Chem. Year 2004, Vol. 4, pp. 330-334; Guidotti et al., J. Mol. Catal. A: Chem., Year 2006, Vol. 250, pp. 218-225; Guidotti et al., Catal. Lett. Year 2008, Vol. 122, pp. 53-56). Sol-gel prepared alumina catalyst showed efficient activity but again required long contact times (24 hr) to achieve 95% conversion of fatty acid methyl esters (Sepulveda et al., Appl. Catal. A: Gen., Year 2007, Vol. 318, pp. 213-217).

References may be made to Journal "Fat Sci. Technol., Year 1995, Vol. 97, pp. 269-273" wherein Debal et al reported the use of $MoO_3$-t-butylhydroperoxide system for the epoxidation of methyl linoleate at 95-115° C. Besides the expected diepoxy derivates dihydroxy tetrahydrofurans were obtained and whose yield reaches up to 75%. The cause of the formation of such large amount of unwanted side products was explained due to the formation of molybdic acid from $MoO_3$ and tert.-butyl hydroperoxide. While the $MoO_3$ or $Mo(CO)_6$-tert.-butyl hydroperoxide/cumylhydroperoxide system is efficient for epoxidation of monoenic fatty esters, it results in a complex mixture of products in the epoxidation of polyenic fatty esters (Debal et al., Lipid/Fett, Year 1993, Vol. 95 (Issue No. 6), pp. 236-239).

References may be made to U.S. Pat. No. 5,081,267, wherein epoxidation of olefinic compounds by reaction with an organic hydroperoxide in the presence of a solid, heterogeneous catalyst comprised of molybdenum oxide finely dispersed in silica or of both molybdenum oxide and titanium oxide finely dispersed in silica has described. The major issue with this catalyst is its deactivation in recyclability studies. The activity of the catalyst drops down from 92 to 20% in the fifth run. The metal content leaches into the reaction medium during the runs. Therefore, a more selective and stable catalyst system even for applications to polyenic fatty acid esters is highly desirable.

References may be made to U.S. Pat. No. 3,634,464, wherein a process of epoxidizing an olefinically unsaturated organic compound with an organic hydroperoxide such as tertiary substituted and unsubstituted-hydrocarbon hydroperoxide e.g. tertiary butyl hydroperoxide, in the presence of a catalyst composition comprising an oxide of molybdenum and a solid inorganic oxide catalyst support containing a major proportion of at least one oxide component selected from silica and alumina, modified by the inclusion therewith of bismuth or certain rare earth metal oxides, said catalyst composition incorporating from about 0.1% to 10% by weight of bismuth or rare earth metal oxide. The catalyst composition is characterized by being essentially insoluble in the epoxidation reaction mixture, providing a heterogenous system has reported. Molybdenum oxide is present in amounts from 0.2% by weight to 5% by weight calculated as molybdenum on the catalyst support. A critical feature of catalyst composition is the presence of a minor proportion of bismuth or certain rare earth oxides as catalyst modifier. It is evident that the modifier plays a substantial role in providing a heterogenous catalyst composition wherein the oxide of molybdenum is not dissolved in the epoxidation reaction mixture, thereby eliminating the requirement of additional apparatus and separation steps for recovery of any soluble molybdenum. Suitable rare earth metal oxide modifiers are oxides of metals having atomic numbers 57 to 71 inclusive, i.e. the lanthanides. Among the oxygen-containing substituted-hydrocarbon olefins which are suitably epoxidized by the process of the invention includes olefinically unsaturated carboxylic acids such as crotonic acid, oleic acid and tetrahydrobenzoic acid; oxygen containing compounds such as soybean oil and corn oil etc. The epoxidation process is conducted at a temperature varying from about 0° C. to about 200° C., preferably from 25 to 200° C., at or above atmospheric pressure, varying from about 1 to 100 atm.

References may be made to Bulletin of the Chemical Society of Japan; Year 1986, Vol. 59, No. 12, pp. 3941-3943, wherein Yasushi Itoi et al. disclose epoxidation of fatty acid esters with 30% aqueous hydrogen peroxide in the presence of a molybdenum oxide-tributyltin chloride on a charcoal catalyst in 2-propanol at 50° C. Such inner olefins as ethyl erucate and ethyl oleate gave yields of 77% and 76%, respectively. Ethyl elaidate, a trans-form of ethyl oleate, was found less reactive (40% yield).

References may be made to Journal "Applied Catalysis A: General Year 2003, Vol. 248, pp. 261-268" and "U.S. Pat. No. 3,351,635", wherein said references disclose the application of homogeneous molybdenum catalysts but then catalyst separation and reuse are issues with those catalyst systems.

In view of the above it is desirable to have an improved, more efficient, selective and reusable solid-catalyst and a process beneficial from environment and economic viewpoints. The process of the present invention using supported molybdenum oxide solid catalyst has all the above-mentioned desirables.

OBJECTIVES OF THE INVENTION

Main objective of the present invention is to provide an improved process for epoxidation of fatty acids, their esters and mixtures thereof.

Another object of the present invention is to provide an efficient, selective, reusable, solid catalyst for preparing epoxy functionalized fatty acids, their esters and mixtures thereof.

Yet another object of the present invention is to provide a process for preparing epoxy functionalized fats with little or no side-products.

Still another object of the present invention is to provide an improved process for preparing epoxy functionalized fats with near complete conversions and high selectivity for epoxides.

SUMMARY OF THE INVENTION

Accordingly, present invention provides an improved process for the epoxidation of mono and polyenic fatty acids, their esters or mixtures thereof using solid catalyst and the said process which comprises contacting mono and polyenic fatty acids, their esters or mixtures thereof with a peroxide in the presence of a solid catalyst for a period in the range of 0.5 to 6 hr at a temperature in the range of 40 to 120° C. followed by separation of the epoxide product from the reaction mixture to obtain mono and poly epoxy functionalized fatty acids, their esters or mixtures thereof wherein the amount of side products of the process is less than 1% and said solid catalyst is a supported group VIB metal oxide, said support comprising silica, alumina and mixtures thereof, optionally with a promoter from group VA wherein the group VIB metal oxide content in the catalyst is 5-20 wt % of support.

In an embodiment of the present invention, fatty acids and their esters are derived from vegetable oils or animal fat.

In another embodiment of the present invention, the fatty acid ester is an alkyl ester, preferably glyceryl or methyl esters of fatty acids.

In yet another embodiment of the present invention, peroxide used is selected from hydrogen peroxide or organic hydroperoxide preferably tert. butyl hydroperoxide.

In yet another embodiment of the present invention, the molar ratio of peroxide to unsaturated bonds in the fatty acids, their esters or mixtures thereof is in the range 1 to 4 preferably in the range 1.1 to 1.5.

In yet another embodiment of the present invention, said solid catalyst used is 1 to 15% by weight with respect to the substrate.

In yet another embodiment of the present invention, said group VA promoter is preferably phosphorous.

In yet another embodiment of the present invention, said catalyst is reusable.

In yet another embodiment of the present invention, the reaction temperature is in the range of 40 to 120° C. preferably at 80-100° C.

In yet another embodiment of the present invention, pressure is in the range of 1 to 10 atm preferably 1-5 atm.

In yet another embodiment of the present invention, time period is in the range of 0.5 to 6 h preferably for 1 to 2 h.

In yet another embodiment of the present invention, amount of side products (diols, furans and oligomers) of the process is less than 1%.

In yet another embodiment of the present invention, the conversion percentage of fatty acids, esters or mixture thereof is in the range of 80 to 100%.

In yet another embodiment of the present invention, epoxide product selectivity is in the range of 97-100%.

In yet another embodiment of the invention, catalyst is a solid and the reaction takes place in a heterogeneous condition, and the solid catalyst can be easily separated from products by centrifugation/filtration for further reuse and the product is selectively the epoxide.

BRIEF DESCRIPTION OF THE DRAWINGS

FIG. 1: $^1$H NMR spectra of epoxidized fatty acid methyl esters (FAME) of soybean oil at different reaction times (reaction conditions as those in Example 11). As the reaction time increases the intensity of proton NMR signals corresponding to protons of double bonds (—CH=CH—) at $\delta$=5.4 ppm, CH$_2$ group next to double bonds (—CH$_2$—CH=CH—CH$_2$—) at $\delta$=2.0 ppm and methylene (=CH—CH$_2$—CH=) at $\delta$=2.7 ppm decrease due to increased conversion of double bonds. New signals corresponding to protons of epoxides (—CHOCH—) at $\delta$=2.9 ppm appear with increasing intensity indicating the formation of epoxides products. No peaks corresponding to side products ($\delta$=3.4 ppm) are observed revealing the selectivity of epoxides as 100%.

DETAILED DESCRIPTION OF THE INVENTION

Present invention provides a process for preparing mono- and poly-epoxy functionalized fatty acids, their esters and mixtures thereof, which comprises contacting mono and polyenic fatty acids, their esters or mixtures thereof with peroxide in the presence of a solid catalyst and separation of the product epoxides from the reaction mixture.

The said solid catalyst is a group VIB metal oxide, preferably molybdenum oxide supported on silica or alumina and mixtures thereof or supports containing these metal oxides or supports containing these oxides along with group VA promoters, preferably phosphorous and exhibits very high catalytic activity for the preparation of epoxy-functionalized fatty acids, their esters and mixtures thereof at atmospheric pressure and moderate temperatures. The catalysts of the present invention are reusable.

The process of the present invention is more efficient and selective, requiring shorter contact times (1 to 4 hrs). Selectivity based on peroxide is greater than 95%. Undesired, side-products are almost negligible. This process can be carried out either in a batch or fixed bed reactor system.

The catalyst was prepared by the known procedures. In a typical preparation of phosphorous modified alumina supported Mo catalyst, 0.35 g of ortho-phosphoric acid (88%) dissolved in 33 ml of water was added drop-wise to 30 g of gamma-alumina (commercial sample) taken in a glass container. It was uniformly mixed and left for 3 to 4 h at 298 K. Then, it was dried for 24 h in an oven at 373 K followed by calcining at 873 K for 6 h. Then, 2.169 g of ammonium heptamolybdate tetrahydrate dissolved in 10 g of water was added drop-wise to 10 g of phosphorous modified alumina prepared as above. It was thoroughly mixed and left for 2 to 3 h at 298 K, dried at 373 K for 24 h and then calcined at 873 K for 6 h. Depending on the requirement; the catalysts can be prepared in the form of powder and shaped into extrudates by the known processes.

Phosphorous modified alumina supported molybdenum oxide catalyst has the physicochemical characteristics listed in Table 1.

TABLE 1

Physicochemical characteristics

| Composition: | |
|---|---|
| $MoO_3$ | 5-20 wt % |
| P | 0.5-2 wt % |
| $Al_2O_3$ | 78-94.5 wt % |
| Textural Characteristics: | |
| Total surface area ($S_{BET}$, $m^2$/g) | 150-210 |
| Average pore diameter (nm) | 6.7-9.2 |
| Total pore volume (cc/g) | 0.3-0.5 |
| Spectral characteristics: | |
| FT-Raman bands ($cm^{-1}$) | 115, 144, 208, 322, 395, 795, 850, 882 |
| Diffuse reflectance UV-visible band (nm) | 233-290 |
| Oxidation state | +6 |
| Crystallite size: | |
| $MoO_x$ | Below the detection limit of X-rays |

EXAMPLES

The following examples are given by way of illustration and therefore should not be construed to limit the scope of the present invention.

Example 1

This example illustrates the preparation of 15% $MoO_x$/$Al_2O_3$—P. In a typical preparation of phosphorous modified alumina supported Mo catalyst, 0.113 g of ortho-phosphoric acid (88%) dissolved in 10 g of water was added drop-wise to 10 g of gamma-alumina (commercial sample) taken in a glass container. It was uniformly mixed and left for 3 h at 298 K. Then, it was dried for 24 h in a hot oven (373 K) followed by calcining at 873 K for 6 h. Then, 2.169 g of ammonium heptamolybdate tetrahydrate dissolved in 10 g of water was added drop-wise to phosphorous modified alumina prepared as above. It was thoroughly mixed and left for 2 h at 298 K, dried 24 h in a hot oven at 373 K and followed by that calcined at 873 K for 6 h.

Example 2

This example illustrates the preparation of 10% $MoO_x$/$Al_2O_3$—P. In a typical preparation of phosphorous modified alumina supported Mo catalyst, 0.113 g of ortho-phosphoric acid (88%) dissolved in 10 g of water was added drop-wise to 10 g of gamma-alumina (commercial sample) taken in a glass container. It was uniformly mixed and left for 3 h at 298 K. Then, it was dried 24 h in a hot oven (373 K) followed by calcining at 873 K for 6 h. Then, 1.364 g of ammonium heptamolybdate tetrahydrate dissolved in 10 g of water was added drop-wise to phosphorous modified alumina prepared as above. It was thoroughly mixed and left for 2 h at 298 K, dried 24 h in a hot oven at 373 K and followed by that calcined at 873 K for 6 h.

Example 3

This example illustrates the preparation of 15% $MoO_x$/$Al_2O_3$. In a typical preparation of unmodified aluminium supported Mo catalyst, 2.169 g of ammonium heptamolybdate tetrahydrate dissolved in 10 g of water was added drop-wise to 10 g of gamma-alumina (commercial sample) taken in a glass container. It was thoroughly mixed and left for 3 h 298 K, dried for 24 h in a hot oven at 373 K and followed by that calcined at 873 K for 6 h.

Example 4

This example illustrates the preparation of 10% $MoO_x$/$Al_2O_3$. In a typical preparation of unmodified aluminium supported Mo catalyst, 1.364 g of ammonium heptamolybdate tetrahydrate dissolved in 10 g of water was added drop-wise to 10 g of gamma-alumina (commercial sample) taken in a glass container. It was thoroughly mixed and left for 3 h at 298 K, dried 24 h in a hot oven at 373 K and followed by that calcined at 873 K for 6 h.

Example 5

This example illustrates the preparation of 15% $MoO_x$/$SiO_2$—$Al_2O_3$. In a typical preparation of aluminosilicate supported Mo catalyst, 0.646 g of ammonium heptamolybdate tetrahydrate dissolved in 10 g of water was added drop-wise to 10 g of aluminosilicate (Si/Al=14) taken in a glass container. It was thoroughly mixed and left for 3 h at 298 K, dried overnight in a hot oven at 373 K and followed by that calcined at 873 K for 6 h.

Example 6

This example illustrates the epoxidation of fatty acid methyl ester of soybean oil over 15% $MoO_x$/$Al_2O_3$—P. The methyl esters of soybean oil (FAME) were prepared by the conventional route by tranesterification of soybean oil with methanol over alkali catalyst. The purity of the esters was confirmed to be 100%. The fatty acid methyl esters composition was determined to be: palmitic acid methyl ester (12 wt %), stearic acid methyl ester (3 wt %), oleic acid methyl ester (27 wt %), linoleic acid methyl ester (52%) and linolenic acid methyl ester (6 wt %). Accordingly the average number of double bonds per methyl ester was found to be 1.49. In a typical epoxidation reaction of FAME, 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 15% $MoO_x/Al_2O_3$—P was added to the contents in the flask. The reaction was conducted for 2 h and the product was analyzed by gas chromatography (Varian 3800) and $^1H$ NMR spectroscopy. Conversion of double bonds=82%; epoxide selectivity=100% and epoxides yield=82%.

Example 7

This example illustrates the epoxidation of fatty acid methyl ester of soybean oil over 10% $MoO_x/Al_2O_3$—P. 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 10% $MoO_x/Al_2O_3$—P was added to the contents in the flask. The reaction was conducted for 2 h and the product was analyzed by gas chromatography (Varian 3800) and $^1H$ NMR spectroscopy. Conversion of double bonds=75.2%; epoxide selectivity=100% and epoxides yield=75.2%.

Example 8

This example illustrates the epoxidation of fatty acid methyl ester of soybean oil over 15% $MoO_x/Al_2O_3$. 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 15% $MoO_x/Al_2O_3$ was added to the contents in the flask. The reaction was conducted for 2 h and the product was analyzed by gas chromatography (Varian 3800) and $^1H$ NMR spectroscopy. Conversion of double bonds=81%; epoxide selectivity=100% and epoxides yield=81%.

Example 9

This example illustrates the epoxidation of fatty acid methyl ester of soybean oil over 10% $MoO_x/Al_2O_3$. 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 10% $MoO_x/Al_2O_3$ was added to the contents in the flask. The reaction was conducted for 2 h and the product was analyzed by gas chromatography (Varian 3800) and $^1H$ NMR spectroscopy. Conversion of double bonds=61.9%; epoxide selectivity=100% and epoxides yield=61.9%.

Example 10

This example illustrates the epoxidation of fatty acid methyl ester of soybean oil over 15% $MoO_x/SiO_2$—$Al_2O_3$. 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 15% $MoO_x/Al_2O_3$ was added to the contents in the flask. The reaction was conducted for 2 h and the product was analyzed by gas chromatography (Varian 3800) and $^1H$ NMR spectroscopy. Conversion of double bonds=74.4%; epoxide selectivity=97% and epoxides yield=72.2%.

Example 11

Figure 1:
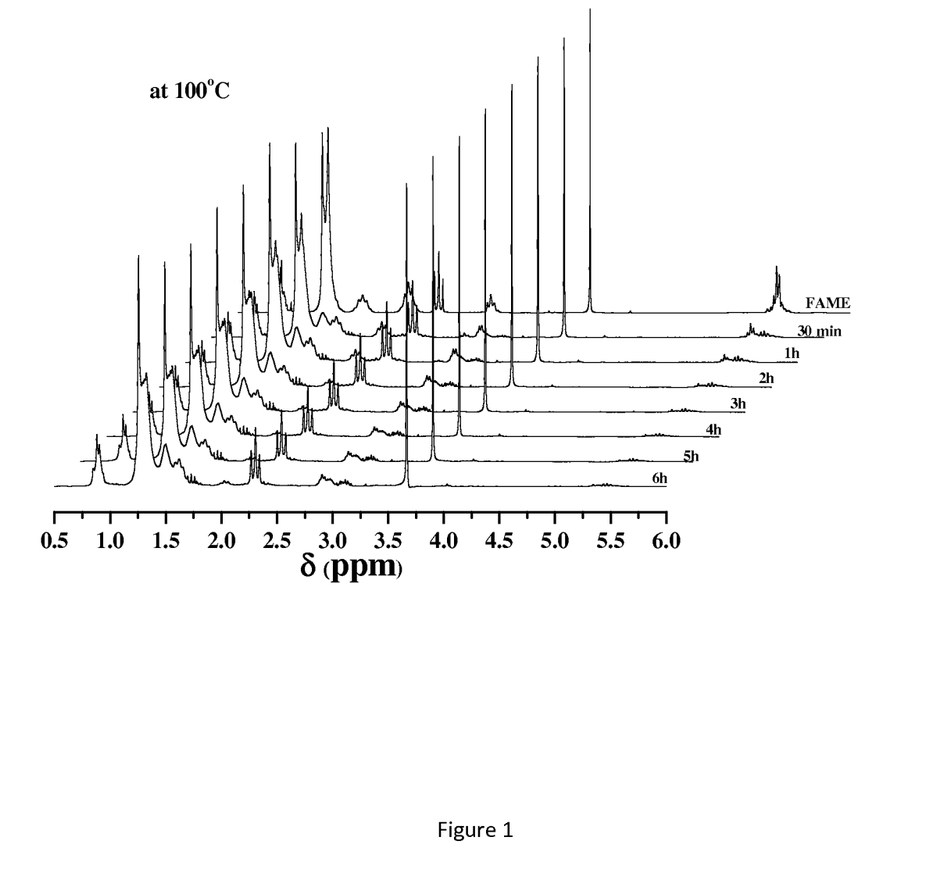

This example illustrates the influence of reaction time on epoxidation of fatty acid methyl ester of soybean oil over 15% $MoO_x/Al_2O_3$. 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 15% $MoO_x/Al_2O_3$ was added to the contents in the flask. The reaction was conducted for 6 h at 100° C. and the product was analyzed by gas chromatography (Varian 3800) and 1H NMR spectroscopy. Table 2 lists the conversion of double bonds, epoxide selectivity and epoxide yield as a function of reaction time.

TABLE 2

Influence of reaction time on the epoxidation of methyl soyate over 15% $MoO_x/Al_2O_3$.

| Reaction time (h) | Double bond conversion (NMR) | Epoxides selectivity (%) | Epoxides yield (%) |
|---|---|---|---|
| 0.5 | 59.8 | 100 | 59.8 |
| 1 | 73.0 | 100 | 73.0 |
| 2 | 81.1 | 100 | 81.1 |
| 3 | 85.6 | 100 | 85.6 |
| 4 | 87.1 | 100 | 87.1 |
| 5 | 87.1 | 100 | 87.1 |
| 6 | 90.1 | 100 | 90.1 |

Example 12

This example illustrates the effect of temperature on the epoxidation of fatty acid methyl ester of soybean oil over 15% $MoO_x/Al_2O_3$. 1 g of FAME was taken in a double-necked glass round-bottom flask fitted with a water-cooled condenser and placed in a temperature-controlled oil bath (80-120° C.). 0.991 g of tert-butyl hydroperoxide (70% aq. TBHP) was extracted into 10 ml of toluene and dried over anhydrous $Na_2SO_4$. It was then added to the above FAME (double bond: TBHP=1:1.5). 0.1 g of 15% $MoO_x/Al_2O_3$ was added to the contents in the flask. The reaction was conducted for 1 h and the product was analyzed by gas chromatography (Varian 3800) and $^1H$ NMR spectroscopy. Table 3 lists the conversion of double bonds; epoxide selectivity and epoxide yield as a function of reaction temperature.

TABLE 3

Influence of reaction temperature on the epoxidation
of methyl soyate over 15% $MoO_x/Al_2O_3$.

| Reaction temperature (° C.) | Double bond conversion (NMR) | Epoxides selectivity (%) | Epoxides yield (%) |
| --- | --- | --- | --- |
| 80 | 51.6 | 100 | 51.6 |
| 90 | 58.1 | 100 | 58.1 |
| 100 | 77.1 | 100 | 77.1 |
| 110 | 86.3 | 100 | 86.3 |
| 120 | 96.1 | 100 | 96.1 |

Example 13

This example illustrates the effect of temperature on the epoxidation of fatty acid methyl ester of soybean oil over 15% $MoO_x/Al_2O_3$—P. 1 g of FAME was taken in a double-necked glass round-bottom flask fitted with a water-cooled condenser and placed in a temperature-controlled oil bath (80-120° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.1 g of 15% $MoO_x/Al_2O_3$—P was added to the contents in the flask. The reaction was conducted for 1 h and the product was analyzed by gas chromatography (Varian 3800) and $^1H$ NMR spectroscopy. Table 4 lists the conversion of double bonds, epoxide selectivity and epoxide yield as a function of reaction temperature.

TABLE 4

Influence of reaction temperature on the epoxidation
of methyl soyate over 15% $MoO_x/Al_2O_3$—P.

| Reaction temperature (° C.) | Double bond conversion (NMR) | Epoxides selectivity (%) | Epoxides yield (%) |
| --- | --- | --- | --- |
| 80 | 53.1 | 100 | 53.1 |
| 90 | 59.5 | 100 | 59.5 |
| 100 | 79.0 | 100 | 79.0 |
| 110 | 87.5 | 100 | 87.5 |
| 120 | 97.1 | 100 | 97.5 |

Example 14

This example illustrates the effect of amount of catalyst on epoxidation of fatty acid methyl ester of soybean oil over 15% $MoO_x/Al_2O_3$. 1 g of FAME was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$.

It was then added to the above FAME (double bond:TBHP=1:1.5). 0 to 0.15 g of 15% $MoO_x/Al_2O_3$ was added to the contents in the flask. The reaction was conducted for 2 h and the product was analyzed by gas chromatography (Varian 3800) and $^1H$ NMR spectroscopy. Table 5 lists the conversion of double bonds; epoxide selectivity and epoxide yield as a function of catalyst amount used in the reaction.

TABLE 5

Influence of the amount catalyst on epoxidation
of methyl soyate over 15% $MoO_x/Al_2O_3$.

| Catalyst amount (g) | Double bond conversion (NMR) | Epoxides selectivity (%) | Epoxides yield (%) |
| --- | --- | --- | --- |
| 0 | 19.7 | 100 | 19.7 |
| 0.01 | 85.2 | 100 | 85.2 |
| 0.02 | 89.4 | 100 | 89.4 |
| 0.05 | 88.3 | 100 | 88.3 |
| 0.07 | 84.2 | 100 | 84.2 |
| 0.10 | 81.1 | 100 | 81.1 |
| 0.15 | 84.7 | 100 | 84.7 |

Example 15

This example illustrates influence of double bond to TBHP ratio on the epoxidation of fatty acid methyl ester of soybean oil over 15% $MoO_x/Al_2O_3$. 1 g of FAME was taken in a double-necked glass round-bottom flask fitted with a water-cooled condenser and placed in a temperature-controlled oil bath (100° C.). Tert-butyl hydroperoxide (70% aq. TBHP) was extracted into 10 ml of toluene and dried over anhydrous $Na_2SO_4$. It was then added to the above FAME with a ratio of double bond:TBHP=1:1 to 1:4). 0.05 g of 15% $MoO_x/Al_2O_3$ was added to the contents in the flask. The reaction was conducted for 1 h and the product was analyzed by gas chromatography (Varian 3800) and $^1H$ NMR spectroscopy. Table 6 lists the conversion of double bonds, epoxide selectivity and epoxide yield as a function of molar ratio of TBHP/double bonds.

TABLE 6

Influence of double bonds:TBHP molar ratio on epoxidation
of methyl soyate over 15% $MoO_x/Al_2O_3$.

| TBHP/double bond molar ratio | Double bond conversion (NMR) | Epoxides selectivity (%) | Epoxides yield (%) |
| --- | --- | --- | --- |
| 1:1 | 58.9 | 100 | 58.9 |
| 1:1.5 | 77.1 | 100 | 77.1 |
| 1:2 | 88.7 | 100 | 88.7 |
| 1:2.5 | 94.8 | 100 | 94.8 |
| 1:3 | 90.0 | 100 | 90.0 |
| 1:4 | 93.4 | 100 | 93.4 |

Example 16

This example illustrates the epoxidation of soybean oil (fatty acid glyceryl esters (99.6 wt %)+oleic acid (0.4 wt %)) over 15% $MoO_x/Al_2O_3$. 0.5 g of soybean oil was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.05 g of 15% $MoO_x/Al_2O_3$ was added to the contents in the flask. The reaction was conducted for 3 h and the product was analyzed by gas chromatography (Varian 3800) and $^1H$ NMR spectroscopy. Conversion of double bonds=82.2%; epoxide selectivity=100% and epoxides yield=82.2%.

Example 17

This example illustrates the epoxidation of oleic acid with two double bonds over 15% $MoO_x/Al_2O_3$. 0.5 g of soybean oil was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.05 g of 15% $MoO_x/Al_2O_3$ was added to the contents in the flask. The reaction was conducted for 3 h and the product was analyzed by gas chromatography (Varian 3800) and $^1H$ NMR spectroscopy. Conversion of double bonds=81.1%; epoxide selectivity=100% and epoxides yield=81.1%.

Example 18

This example illustrates the epoxidation of oleic acid over 15% $MoO_x/Al_2O_3$—P. 0.5 g of soybean oil was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.05 g of 15% $MoO_x/Al_2O_3$—P was added to the contents in the flask. The reaction was conducted for 3 h and the product was analyzed by gas chromatography (Varian 3800) and $^1H$ NMR spectroscopy. Conversion of double bonds=85.0%; epoxide selectivity=100% and epoxides yield=85%.

Example 19

Figure 2:
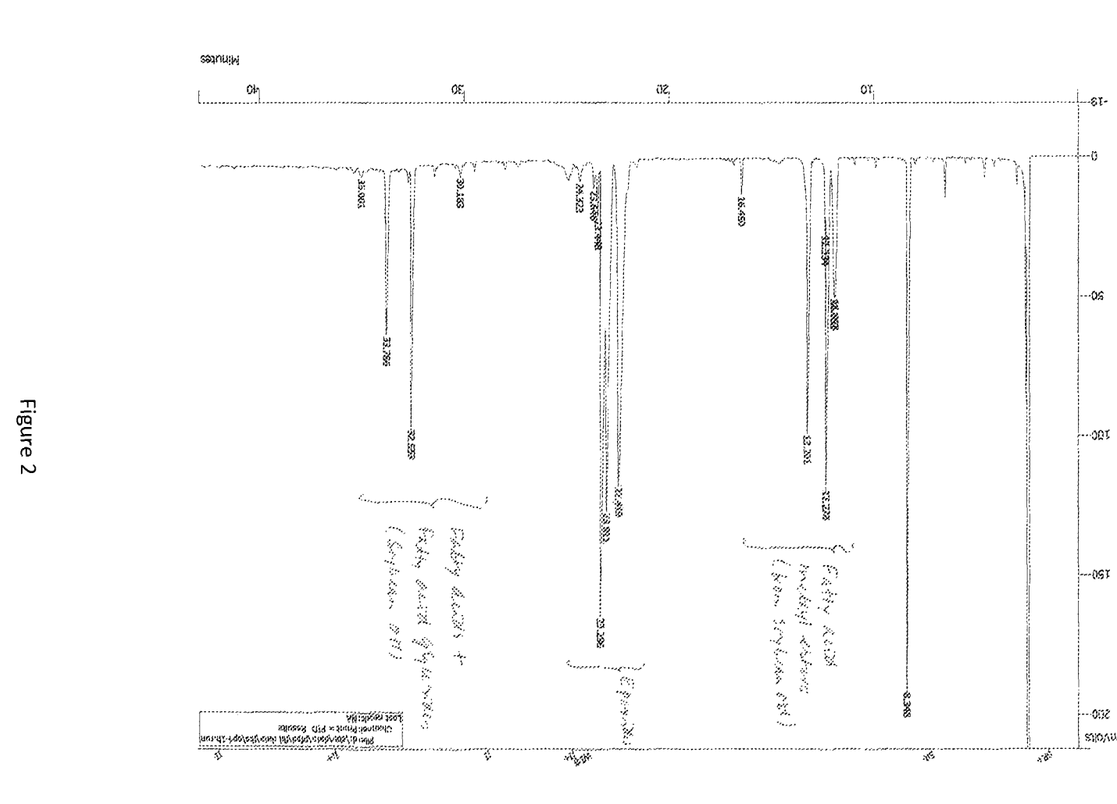
FIG. 2: GC chart of reaction mixture (Example 19) showing absence of side products.

This example illustrates the epoxidation of a mixture of oleic acid and fatty acid methyl and glyceryl esters derived from soybean oil over 15% $MoO_x/Al_2O_3$—P. 0.5 g of fatty acid (oleic acid) and soybean methyl and glyceryl esters mixture was taken in a double-necked glass round-bottom flask fitted with a water-cooled condenser and placed in a temperature-controlled oil bath (100° C.). 0.991 g of tert-butyl hydroperoxide (70% aq. TBHP) was extracted into 10 ml of toluene and dried over anhydrous $Na_2SO_4$. It was then added to the above FAME (double bond:TBHP=1:1.5). 0.05 g of 15% $MoO_x/Al_2O_3$—P was added to the contents in the flask. The reaction was conducted for 3 h and the product was analyzed by gas chromatography (Varian 3800) and $^1H$ NMR spectroscopy. Conversion of double bonds=81.2%; epoxide selectivity=100% and epoxides yield=81.2%.

Example 20

This example illustrates the reusability of 15% $MoO_x/Al_2O_3$—P in the epoxidation of fatty acid methyl ester of soybean oil. The reaction was conducted for 1 h at 120° C. as described in the example 13. At the end of the reaction the catalyst was recovered by centrifugation/filtration and then reused in another batch of reaction conducted in a similar manner. Such a recycle was continued for 5 times and the results obtained are listed in different recycle experiments are listed in Table 7.

TABLE 7

Catalyst recyle/reusability study: Epoxidation of methyl soyate over 15% $MoO_x/Al_2O_3$—P.

| Number of recycles | Double bond conversion (NMR) | Epoxides selectivity (%) | Epoxides yield (%) |
|---|---|---|---|
| Fresh | 97.1 | 100 | 97.1 |
| 1$^{st}$ recycle | 97.0 | 100 | 97.0 |
| 2$^{nd}$ recycle | 97.0 | 100 | 97.0 |
| 3$^{rd}$ recycle | 96.5 | 100 | 96.5 |
| 4$^{th}$ recycle | 95.8 | 100 | 95.8 |
| 5$^{th}$ recycle | 95.0 | 100 | 100 |

ADVANTAGES OF THE INVENTION

The catalyst of the present invention is reusable and thereby reduces the processing steps and makes the process economical and environmental friendly.

The epoxidation process of the present invention is equally applicable to both mono and polyenic fatty compounds and their mixtures.

Another advantages feature of the invention is that the unwanted side products in the reaction are less than 1%.

The invention claimed is:

1. An improved process for the epoxidation of mono and polyenic fatty acids, their esters or mixtures thereof using solid catalyst and the said process which comprises contacting mono and polyenic fatty acids, their esters or mixtures thereof with a peroxide in the presence of a solid catalyst for a period in the range of 0.5 to 6 hr at a temperature in the range of 40 to 120° C. followed by separation of the epoxide product from the reaction mixture to obtain mono and poly epoxy functionalized fatty acids, their esters or mixtures thereof wherein the amount of side products of the process is less than 1% and said solid catalyst is a supported group VIB metal oxide, said support comprising silica, alumina and mixtures thereof, optionally with a promoter from group VA wherein the group VIB metal oxide content in the catalyst is 5-20 wt % of support.

2. The improved process as claimed in claim 1, wherein fatty acids and their esters are of vegetable oils or animal fat origin.

3. The improved process as claimed in claim 1, wherein the fatty acid ester is an alkyl ester.

4. The improved process as claimed in claim 1, wherein peroxide used is selected from hydrogen peroxide and organic hydroperoxide.

5. The improved process as claimed in claim 1, wherein the molar ratio of peroxide to unsaturated bonds in the fatty acids, their esters or mixtures thereof is in the range 1 to 4.

6. The improved process as claimed in claim 1, wherein said solid catalyst used is 1 to 15% by weight with respect to the substrate.

7. The improved process as claimed in claim 1, wherein said group VA promoter is phosphorous.

8. The improved process as claimed in claim 1, wherein said catalyst is reusable.

9. The improved process as claimed in claim 1, wherein the reaction temperature is in the range of −80-120° C.

10. The improved process as claimed in claim 1, wherein pressure is in the range of 1 to 10 atm.

11. The improved process as claimed in claim 1, wherein time period is in the range of 0.5 to 6 h.

12. The improved process as claimed in claim 1, wherein the side products are diols, furans and oligomers.

13. The improved process as claimed in claim 1, wherein the conversion percentage of fatty acids, esters or mixture thereof is in the range of 80 to 100%.

14. The improved process as claimed in claim 1, wherein epoxide product selectivity is in the range of 97-100%.

15. The improved process as claimed in claim 1, wherein the group VIB metal oxide is molybdenum oxide.

16. The improved process as claimed in claim 3, wherein the alkyl ester is glyceryl or methyl ester of fatty acids.

17. The improved process as claimed in claim 5, wherein the organic hydroperoxide is tert-butyl hydroperoxide.

18. The improved process as claimed in claim 5, wherein the molar ratio of peroxide to unsaturated bonds in the fatty acids, their esters or mixtures thereof is in the range 1.1 to 1.5.

19. An improved process for the epoxidation of mono and polyenic fatty acids, their esters or mixtures thereof using solid catalyst and the said process which comprises contacting mono and polyenic fatty acids, their esters or mixtures thereof with a peroxide in the presence of a solid catalyst for a period in the range of 0.5 to 6 hr at a temperature in the range of 40 to 120° C. followed by separation of the epoxide product from the reaction mixture to obtain mono and poly epoxy functionalized fatty acids, their esters or mixtures thereof wherein the amount of side products of the process is less than 1% and said solid catalyst is a supported group VIB metal oxide, said support comprising silica, alumina and mixtures thereof, optionally with a promoter from group VA wherein the group VIB metal oxide content in the catalyst is 5-20 wt % of support and wherein epoxide product selectivity is in the range of 97-100%.

20. The improved process as claimed in claim 19, wherein fatty acids and their esters are of vegetable oils or animal fat origin.

21. The improved process as claimed in claim 19, wherein peroxide used is selected from hydrogen peroxide and organic hydroperoxide.

22. The improved process as claimed in claim 19, wherein said solid catalyst used is 1 to 15% by weight with respect to the substrate.

23. The improved process as claimed in claim 19, wherein said group VA promoter is phosphorous.

24. The improved process as claimed in claim 19, wherein said catalyst is reusable.

25. The improved process as claimed in claim 19, wherein pressure is in the range of 1 to 10 atm.

26. The improved process as claimed in claim 19, wherein the group VIB metal oxide is molybdenum oxide.

* * * * *